United States Patent
Ramachandran et al.

(10) Patent No.: US 11,311,643 B2
(45) Date of Patent: Apr. 26, 2022

(54) FIBRIN AND/OR DIALDEHYDE STARCH HYDROLYSATE MATERIALS, AND PREPARATION AND USE THEREOF

(71) Applicant: Cook Biotech Incorporated, West Lafayette, IN (US)

(72) Inventors: Niraj Ramachandran, Sharon, MA (US); Brooke Lynn Davisson, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 54 days.

(21) Appl. No.: 16/156,340

(22) Filed: Oct. 10, 2018

(65) Prior Publication Data

US 2019/0117825 A1  Apr. 25, 2019

Related U.S. Application Data

(63) Continuation of application No. PCT/US2017/027044, filed on Apr. 11, 2017.

(60) Provisional application No. 62/320,854, filed on Apr. 11, 2016.

(51) Int. Cl.

| | |
|---|---|
| *A61K 38/00* | (2006.01) |
| *A61L 24/04* | (2006.01) |
| *A61L 24/08* | (2006.01) |
| *A61L 24/10* | (2006.01) |
| *A61L 24/00* | (2006.01) |
| *B29C 39/00* | (2006.01) |

(52) U.S. Cl.
CPC ............. *A61L 24/106* (2013.01); *A61K 38/00* (2013.01); *A61L 24/0005* (2013.01); *A61L 24/0015* (2013.01); *A61L 24/0031* (2013.01); *A61L 24/043* (2013.01); *A61L 24/08* (2013.01); *B29C 39/003* (2013.01); *A61L 2400/04* (2013.01); *B29K 2003/00* (2013.01)

(58) Field of Classification Search
CPC .............. A61L 24/106; A61L 24/0005; A61L 24/0015; A61L 24/0031; A61L 24/043; A61L 24/08; A61L 2400/04; A61K 38/00; B29C 39/003; B29K 2003/00; A61P 7/04
See application file for complete search history.

(56) References Cited

U.S. PATENT DOCUMENTS

| | | | |
|---|---|---|---|
| 6,599,515 B1 * | 7/2003 | Delmotte | A61B 17/00491 424/422 |
| 2009/0326577 A1 * | 12/2009 | Johnson | A61B 17/0057 606/213 |

OTHER PUBLICATIONS

Chatzistavrou et al., Journal of Non-Crystalline Solids, 2016, vol. 432, p. 143-149, available online Apr. 1, 2015.*
Dohan et al., Oral Surg Oral Med Oral Pathol Oral Radiol Endod, 2006, vol. 101, p. E37-44.*
hopkinsmedicine.org, platelet counts in blood, 1 page, downloaded from google on Sep. 14, 2020.*

* cited by examiner

*Primary Examiner* — Kade Ariani
(74) *Attorney, Agent, or Firm* — Woodard, Emhardt, Henry, Reeves and Wagner LLP (57) ABSTRACT

Various compositions of matter, methods of making compositions of matter, and methods of using compositions of matter, e.g. for inducing hemostasis, are disclosed. In some embodiments, a starting fibrin material is subjected to controlled hydrolysis, desirably base-catalyzed, to prepare a fibrin hydrolysate material with increased water sorption capacity. Such fibrin hydrolysate materials, alone or combined with one or more additional substances, can be used in the preparation of hemostasis promoting foams, powders or gels. In some embodiments, a starting dialdehyde starch material is subjected to controlled hydrolysis to prepare a dialdehyde starch hydrolysate material. Such dialdehyde starch hydrolysate materials, alone or combined with one or more additional substances, in some cases combined with a fibrin hydrolysate material, can be used in the preparation of hemostasis promoting foams, powders or gels.

24 Claims, 3 Drawing Sheets

FIBRIN AND/OR DIALDEHYDE STARCH HYDROLYSATE MATERIALS, AND PREPARATION AND USE THEREOF

REFERENCE TO RELATED APPLICATION

This application is a continuation of International Application No. PCT/US2017/027044 filed Apr. 11, 2017 which claims the benefit of priority of U.S. Provisional Patent Application No. 62/320,854 filed Apr. 11, 2016, each of which is hereby incorporated herein by reference in its entirety.

BACKGROUND

In certain aspects, the present disclosure relates to methods and materials that are useful for facilitating hemostasis, including methods and materials involving the use of preparations that include fibrin or derivatives thereof and/or dialdehyde starch or derivatives thereof.

Coagulation of blood, sometimes called clotting, is a process during which liquid blood thickens to form a gel or solid clot. This process may result in termination of blood loss from site of damage, also called hemostasis.

Coagulation of blood and the concomitant hemostasis is highly conserved throughout biology, with the human cascade system perhaps being the most studied in animal physiology. In the human cascade leading to hemostasis, prothrombin is transformed to thrombin by calcium ions ($Ca^{2+}$) and thromboplastins. Thrombin catalyzes the conversion of soluble fibrinogen molecules to insoluble fibrin molecules, which often form strands. Fibrin strands help to adsorb platelets from blood and form a plug which helps to mechanically form a clot and reduce blood loss from an injury.

Oftentimes, for example in conjunction with surgery or other events causing injury and bleeding, it is desired to apply treatment to the site of bleeding to facilitate hemostasis. Treatments can involve the application of pressure to the site of bleeding and/or the application of a hemostatic material to the site of bleeding. Despite prior work in the area of hemostatic materials, there remain needs for new materials that promote hemostasis, as well as for methods of their preparation and use.

SUMMARY

In certain aspects, the present disclosure relates to materials derivable by modification of fibrin-containing starting materials, that can be useful for example as hemostatic agents, and methods related thereto. The modification can result in a modified material that has an increased water sorption capacity relative to the fibrin-containing starting material. Accordingly, in certain embodiments, provided are methods for making a hemostasis promoting material that include subjecting a fibrin-containing starting material to hydrolysis conditions so as to form a fibrin hydrolysate material that can have an increased sorption capacity for water at a pH of 7 relative to the fibrin-containing starting material. In preferred forms the hydrolysis conditions comprise contacting the fibrin starting material with a basic liquid medium and/or the fibrin hydrolysate material exhibits a sorption capacity for water at a pH of 7 of greater than about 10 times its dry weight. The fibrin-containing starting material can be a clot material, for example a clot material prepared by clotting a lysed platelet concentrate. The lysed platelet concentrate can be one that has been formed by lysing a platelet concentrate (preferably an apheresed platelet unit) having a platelet concentration of about $10^8$ platelets per ml or greater. The fibrin hydrolysate material, alone or combined with one or more other materials, can be incorporated into products of various forms, including for example powders, foams, or gels. These products preferably incorporate the fibrin hydrolysate material in a form that actively promotes clotting, for example exhibiting a capacity, when saturated with water, to thicken or gel when contacted with thrombin ("thrombin-reactive" fibrin hydrolysate) and/or a calcium salt ("calcium-reactive" fibrin hydrolysate) such as calcium chloride. In some variants, a castable preparation containing the fibrin hydrolysate material is cast into a mold and dried in the mold, for example by lyophilization, to form a solid body. The castable preparation is desirably free from added chemical crosslinkers in some embodiments. Products prepared or preparable by these or other methods disclosed herein are also contemplated as embodiments disclosed herein.

In additional embodiments, provided are medical hemostatic compositions or other compositions that include a water-insoluble, water-swellable fibrin hydrolysate material, a water-insoluble, water-swellable dialdehyde starch material, or a combination thereof. The compositions can, for example, be in the form of a powder or foam, or a flowable aqueous medium such as an aqueous gel. Desirably, the fibrin hydrolysate material exhibits a sorption capacity for water at a pH of 7 of greater than about 10 times its dry weight. In some preferred forms, the fibrin hydrolysate material has not been crosslinked with a chemical crosslinker and/or exhibits a capacity to actively promote clotting, for example exhibiting a capacity, when saturated with water, to thicken or gel when contacted with thrombin and/or a calcium salt such as calcium chloride. The composition can, in addition to the fibrin hydrolysate material, dialdehyde starch hydrolysate material, or combination thereof, also comprise one or more other substances, and in certain forms also incorporates at least one biologic polymer, for example collagen, that is not fibrin.

In other embodiments, provided herein are methods for making a hemostasis promoting material, comprising subjecting a starting dialdehyde starch material to a heated aqueous medium so as to form a dialdehyde starch hydrolysate material. The dialdehyde starch hydrolysate material can be a water-insoluble, water-swellable dialdehyde starch hydrolysate material. In preferred aspects, the heated aqueous medium has an acidic pH, for example less than about 5.

In further embodiments, provided are methods for treating a human or other animal patient which include applying to the patient a composition as disclosed herein. The method can in preferred forms be a method for promoting hemostasis at a site of bleeding in the patient.

Additional disclosed embodiments, as well as features and advantages attendant thereto, will be apparent from the descriptions herein.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications, and such further applications of the principles of the invention as described herein being contemplated as would normally occur to one skilled in the art to which the invention relates.

As disclosed above, some aspects of the present disclosure relate to fibrin hydrolysate materials, products incorporating the fibrin hydrolysate materials, and methods of their manufacture and use. Fibrin hydrolysate materials can be prepared by hydrolysis of a fibrin-containing material, preferably by contact with a liquid medium having a basic pH. The extent of hydrolysis can be controlled to provide a water-insoluble, water-swellable fibrin hydrolysate material. The water-swellable fibrin hydrolysate material can have an absorptive capacity for water that is increased relative to the fibrin material prior to the hydrolysis, preferably increased by at least 100% (i.e. the fibrin hydrolysate material has a sorptive capacity for water that is at least two times that of the fibrin material prior to the hydrolysis). In other aspects, the present disclosure relates to dialdehyde starch hydrolysate materials, products incorporating the dialdehyde starch hydrolysate materials (potentially in combination with a fibrin hydrolysate material as described herein), and methods of their manufacture and use. Dialedhyde starch hydrolysate materials can be prepared by hydrolysis of a dialdehyde starch material. The extent of hydrolysis can be controlled to provide a water-insoluble, water-swellable dialedhyde starch hydrolysate material.

The following terms have the indicated meanings as used herein.

"Fibrin" means an insoluble fibrous protein formed from fibrinogen.

"Fibrin hydrolysate material" means a reaction product obtained by subjecting fibrin to hydrolysis.

"Water-insoluble, water-swellable fibrin hydrolysate material" means a fibrin hydrolysate material that is insoluble in, but that absorbs water and swells when immersed in, water at pH 7 at 20° C.

"Dialdehyde starch" means a starch that has been oxidized (typically in the presence of periodate) to convert repeating glucose units to repeating dialdehyde groups of the formula:

"Dialdehyde starch hydrolysate material" means a reaction product obtained by subjecting a dialdehyde starch to hydrolysis.

"Water-insoluble, water-swellable dialdehyde starch hydrolysate material" means a dialdehyde starch hydrolysate material that is insoluble in, but that absorbs water and swells when immersed in, water at pH 7 at 20° C.

A variety of fibrin-containing starting materials can be used in processes of and in preparing products of the present disclosure. Illustratively, the fibrin-containing starting material can be a gel formed by clotting a fibrinogen-containing material. The fibrinogen-containing material may be blood or a blood fraction, e.g. a platelet-enriched blood fraction, from a single donor or as a pooled material from multiple donors. Platelet-enriched blood fractions, or lysates thereof, are preferred for use as the fibrinogen-containing material to be clotted to form a fibrin-containing gel starting material. In certain embodiments, the platelet-enriched blood fraction is platelet rich plasma ("PRP"), which may be prepared by centrifuging blood or a blood fraction to separate a platelet-enriched plasma supernatant from a cell pellet, and then collecting the supernatant. In other embodiments, the platelet-enriched blood fraction is a platelet concentrate prepared by apheresis of blood or a blood fraction. Such apheresed platelet concentrate units are commonly collected from human donors for potential administration to patients in need of platelet function. In current practice, these apheresed platelet concentrate units are considered expired and no longer administrable to patients as platelet units after several days, for example after five to seven days. In particularly preferred forms, expired apheresed platelet concentrate units, or lysates thereof that can optionally be prepared by one or more freeze-thaw cycles, are used as a fibrinogen-containing material herein to be clotted to prepare a starting fibrin-containing gel material for use herein.

The concentration of platelets in the platelet-enriched fraction is preferably at least $1 \times 10^5$ platelets/ml and more preferably at least $1 \times 10^7$ platelets/ml. Particularly preferred are platelet-enriched fractions, especially apheresed platelet concentrate units (expired or non-expired), that have a concentration of platelets in the range of about $1 \times 10^8$ to about $1 \times 10^{12}$ platelets/ml. The apheresed platelet concentrate units or other platelet-enriched fraction, or other fibrinogen-containing material to be clotted, may also contain one or more anticoagulant substances, including for example ethylenediaminetetraacetic acid (EDTA), heparin, and/or citrate. These anticoagulants may be removed before clotting, or the clotting conditions can be selected to overcome the effect of the anticoagulant(s), for example by adding an excess of an exogenous clotting agent such as thrombin or a calcium salt.

The fibrinogen-containing material that will be clotted to form the fibrin-containing gel starting material can also contain other components or fractions of blood, including for example, serum, plasma, platelets or platelet membrane materials, and/or platelet-derived factors such as growth factors, cytokines or clotting factors. When a platelet-enriched fraction such as PRP or an apheresis platelet concentrate unit, or a lysate thereof, is used in the preparation of a fibrin-containing gel, such fraction or lysate is desirably substantially depleted of cells other than platelets, for example wherein about 98% or more of the cells of the enriched fraction are platelets. In such enriched fractions, there may be cells other than platelets present (e.g. cells including red blood cells and/or white blood cells), for example constituting less than 2% of the cells present in the enriched fraction.

A fibrinogen-containing material can be converted to a fibrin-containing gel by any suitable method. Various modes of clotting the fibrinogen-containing material are known and can be used. These include, for example, clotting by addition of exogenous calcium, exogenous thrombin, or combinations thereof. It is preferred to clot the fibrinogen-containing starting material by addition of a calcium salt in the absence of added exogenous thrombin, or at least in the substantial absence of added exogenous thrombin (i.e. less than about 0.2 US units of exogenous thrombin per milliliter of the fibrinogen-containing starting material having been added, more preferably less than 0.1 US units per milliliter). For US units of thrombin activity, reference is made to Whitton et al., *Thromb Haemost.* 2005 February; 93(2):261-6. Clotting induced by adding calcium has been found useful in providing a less crosslinked fibrin-containing gel (than exogenous thrombin-induced clotting), which is more advantageous for hydrolysis processing to provide a fibrin hydrolysate product as described herein. Additionally, such calcium-induced clotting proceeds acts in the clotting pathway at a different location than exogenous thrombin-induced clotting, and thus impacts the content of residual clotting factors in the prepared fibrin-containing gel. For example, because thrombin but not calcium converts fibrinogen to fibrin monomer, clotting the fibrinogen-containing material without the addition of exogenous thrombin may be carried out so as to leave more residual fibrinogen within the clotted fibrin-containing gel than if exogenous thrombin is added. As well, because thrombin in involved in the conversion of factor VIII to VIIIa, the use of calcium addition rather than exogenous thrombin addition may leave more residual factor VIII in the clotted gel material. As well, because thrombin converts factor VIII to factor VIIIa, and factor VIIIa is involved in the crosslinking of the fibrin polymer, consistent with the discussions above, clotting through the addition of calcium rather than exogenous thrombin may be carried out so as to provide a less crosslinked and softer clotted gel mass to be subjected to hydrolysis conditions. These differences in the fibrin-containing gel material to be subjected to the hydrolysis conditions can then also lead to differences in the fibrin hydrolysate material.

A prepared fibrin-containing gel starting material can include entrained materials derived from the fibrinogen-containing material. For example, it may contain entrained platelet membrane materials and/or entrained platelet-derived factors. These entrained platelet-derived factors can include for example fibrin monomers, fibrinogen, transforming growth factor-beta1 (TGF-beta1), platelet-derived growth factor (PDGF), vascular endothelial growth factor (VEGF), and/or endothelial growth factor (EGF). The prepared fibrin-containing starting material can be used immediately in a hydrolysis process as described herein or alternatively can be stored in any suitable condition. For example, the fibrin-containing gel can be stored wet under cooled conditions, frozen, or dried (e.g. lyophilized). If stored in a dried state the fibrin-containing gel material can be rehydrated upon or before subjecting it to a hydrolysis process as described herein.

In accordance with aspects herein, the fibrin-containing gel material will be subjected to hydrolysis conditions. These conditions will be controlled to achieve a partial hydrolysis of the material so as to result in a water-insoluble, water-swellable fibrin hydrolysate product. The hydrolysis conditions can be catalyzed conditions, for example including acid catalyzed hydrolysis or base catalyzed hydrolysis, or combinations thereof. Base catalyzed hydrolysis conditions are preferred, for example by contacting the fibrin-containing gel with an aqueous medium having a pH in the range of about 9 to 14, and more preferably in the range of about 10 to about 13.5. If used, acid catalyzed conditions can include contacting the fibrin-containing gel material with an aqueous medium having a pH of about 2 to about 5.5. When used herein, the term "base" generally refers to a Bronsted base, i.e., a compound that can accept a proton ($H^+$) unless otherwise contradicted by context. Common examples of bases include, but are not limited to, strong bases, i.e., bases that completely dissociate in aqueous solution such as, but not limited to, sodium hydroxide (NaOH) and potassium hydroxide (KOH). When used herein, the term "acid" generally refers to a Bronsted acid, i.e., a compound that can donate a proton ($H^+$) unless otherwise contradicted by context. Common examples of acids include, but are not limited to, strong acids, i.e., acids that completely dissociate in aqueous solution such as, but not limited to hydrochloric acid (HCl), sulfuric acid ($H_2SO_4$), phosphoric acid ($H_3PO_4$), weak acids and/or organic acids including, but not limited to carboxylic acids such as acetic acid (HOAc).

The temperature of the hydrolysis conditions will also impact the progress of the hydrolysis of the fibrin-containing gel material. A liquid hydrolysis medium contacted with fibrin-containing gel can be cooled, for example at a temperature in the range of about 1° C. to about 20° C. and more preferably in the range of about 0° C. to about 15° C., to slow the progress of the hydrolysis and thereby enhance the ability to control the level of hydrolysis of the fibrin-containing gel that is attained. In addition or alternatively, the time period over which the fibrin-containing gel material is contacted with a hydrolysis medium can be used to control the extent of hydrolysis. In preferred hydrolysis processes, the gel is contacted with the hydrolysis medium for a period of time in the range of about 10 minutes to about 10 hours, more preferably about 20 minutes to about 2 hours, and even more preferably about 30 minutes to about 90 minutes. It will be understood, however, that other times and temperatures may be used in broader aspects of the present disclosure, and that these and other conditions affecting the rate of hydrolysis can be controlled to provide fibrin hydrolysate materials with the properties discussed herein.

In this regard, as discussed above, the hydrolysis process is controlled so as to result in a fibrin hydrolysate that is water-insoluble but water-swellable. The hydrolysis processing will also preferably be conducted so as to yield a substantial percentage by weight of the starting fibrin-containing gel material as a water-insoluble, water-swellable fibrin hydrolysate material. For example, the hydrolysis process can yield at least 50 percent by weight of the starting gel material as a water-insoluble, water-swellable fibrin hydrolysate material, more preferably at least 60 percent, and even more preferably at least 70 percent. In particularly preferred processes, at least 90 percent by weight of the starting fibrin-containing gel material will be yielded as the water-insoluble, water-swellable fibrin hydrolysate product. The hydrolysis process is controlled to achieve such yield. During the hydrolysis reaction, it is preferred that the above-stated percentages of the fibrin-containing starting material remain as insoluble material in the hydrolysis medium throughout the hydrolysis reaction. If the hydrolysis processing conditions are too harsh and/or too long, too much or all of the starting fibrin-containing material will be rendered soluble in the hydrolysis medium, disrupting or reducing the desired gel-forming capacities and other potential properties of the controlled hydrolysate material discussed herein.

The hydrolysis process can be terminated in any suitable fashion. For example, where an acid-catalyzed or base-catalyzed hydrolysis is conducted, the liquid hydrolysis medium can be neutralized by the addition of buffers, or acids (for base-catalyzed hydrolysis) or bases (for acid-catalyzed hydrolysis). Additionally or alternatively, the hydrolysis medium can be exchanged for a rinse medium, for example by decanting the hydrolysis medium from the fibrin hydrolysate material, and the fibrin-hydrolysate material rinsed multiple times to terminate the hydrolysis process.

During the hydrolysis process, the fibrin-containing gel and forming or formed fibrin hydrolysate can swell to some extent relative to the starting gel material. In preferred processes the swelling that occurs during hydrolysis is much less than that which occurs in a later step in which the fibrin hydrolysate material is incubated in a relatively neutral aqueous medium, as discussed below.

As well, the hydrolysis conditions, neutralization, decanting and/or rinsing steps can deactivate and/or remove components of the starting material other than fibrin or fibrin hydrolysate, for example growth factors, cytokines, clotting factors and/or polymerizable fibrin monomers that may occur as platelet derived components. Such deactivation and/or removal can be partial in nature and thus leave some of these components as residuals in the recovered fibrin hydrolysate product. When present, polymerizable fibrin monomers can polymerize to form fibrin, for example on contact with calcium chloride or other appropriate substances, such as blood (e.g. blood at a site of bleeding to be treated).

After completion of the hydrolysis process, the resulting fibrin hydrolysate product is preferably allowed to incubate in an aqueous solution (e.g. water) at substantially neutral pH (e.g. about pH 6 to about pH 8, preferably about 6.8 to 7.5) for a period of time, for example at least about 1 hour, e.g. in the range of 1 hour to 36 hours. During this period, the fibrin hydrolysate material absorbs water and swells, which can be noted by an increase in the volume of the fibrin hydrolysate material as it incubates in the aqueous medium, for example swelling to at least 150% of its volume at the completion of the hydrolysis conditions. This property of the fibrin hydrolysate material, a capacity to swell very substantially, differentiates it from the non-hydrolyzed fibrin gel starting material, which will swell to a lesser extent under corresponding conditions. The capacity of the fibrin hydrolysate material to swell can be characterized in terms of a sorption capacity for water. In preferred forms, the fibrin hydrolysate material will have a sorption capacity for water that is greater than about 2 times that of the fibrin-containing gel starting material, and more preferably greater than about 4 times that of the fibrin-containing gel starting material. In addition or alternatively, the fibrin hydrolysate materials can exhibit a sorption capacity for water at pH 7 and a temperature of 20° C. of greater than about 10, or greater than about 20, times its weight (considered on a dry weight basis). In some preferred forms the fibrin hydrolysate material will exhibit a sorption capacity for water at pH 7 and a temperature of 20° C. of about 10 to about 80, or about 15 to about 60, times its weight (considered on a dry weight basis).

As noted above, the fibrin hydrolysate material can contain components residual from the fibrin-containing gel starting material, such as growth factors, cytokines, and/or clotting factors, which can optionally be platelet derived components. In addition or alternatively, the fibrin hydrolysate material can exhibit a capacity to actively clot when contacted with calcium, thrombin, or a combination thereof. This active clotting exhibited by the fibrin hydrolysate material can be observed by an increase in the viscosity of a suspension or gel of the fibrin hydrolysate material when contacted with calcium (e.g. in the form of calcium chloride salt) and/or thrombin.

The fibrin hydrolysate material can be used immediately in the preparation of further products, for example hemostatic products, or can be stored wet or dry (e.g. lyophilized form) prior to further use. The fibrin hydrolysate material may also be modified for incorporation into products. For example, it may be subjected to shearing forces, for example by blending with a rotating blade blender, to shear the material and/or aerate the material, before its use in downstream processing. In certain aspects the fibrin hydrolysate material in a hydrated, swollen condition is sheared and aerated to prepare an aerated gel, which can be used in or as a gel product or which can be incorporated as or in a castable preparation that is charged to a mold and dried, e.g. by lyophilization, to form a foam body. The foam body may, for example, be in the form of a sheet, block or cylinder.

The fibrin hydrolysate material can be used in any suitable amount or fashion in the preparation of products. In certain forms, the fibrin hydrolysate material will be used in the preparation of formed bodies (e.g. foams) or powders that contain the fibrin hydrolysate material, or in the preparation of gels. Such bodies, powders or gels, or other products, can be constituted entirely of the fibrin hydrolysate material or can include the fibrin hydrolysate material in combination, such as in admixture, with one or more other materials. In certain embodiments, the fibrin hydrolysate material is incorporated in a formed body or other product in combination with a matrix-forming material other than the fibrin hydrolysate material. Such a matrix-forming material can include for example one or more natural and/or synthetic polymers. As natural polymers candidates include collagen, gelatin, and other matrix-forming materials prepared synthetically or derived from tissues of plants or animals. In preferred forms, the natural or synthetic polymer or polymers included with the fibrin hydrolysate will be biocompatible and/or bioabsorbable. In certain forms, the fibrin hydrolysate material is incorporated in a formed body such as a foam body along with a matrix-forming natural or synthetic polymeric material, with such matrix-forming polymeric material in some variants of the invention being an expanded collagenous extracellular matrix (ECM) or other collagen-containing material. The expanded collagenous ECM or other collagen-containing material can be prepared, for example, as described in U.S. Patent Application Publication No. 20090326577 of Cook Biotech Incorporated, published Dec. 31, 2009, which is hereby incorporated herein by reference. In such preparation, the ECM or other collagen-containing material can be formed by contact with a basic liquid medium under conditions and for a period of time effective to expand the starting collagen-containing tissue material to provide the expanded material, e.g. with the expanded collagen-containing tissue material having a volume that is at least 150% of that of the starting ECM or other collagen-containing tissue material. Expanded submucosal ECM materials are preferred for these purposes. When any of these or another matrix-forming material other than the fibrin hydrolysate material is used, it can be used in a dry weight ratio of about 90:10 to about 10:90 relative to the fibrin hydrolysate material, more preferably about 70:30 to about 30:70, and in certain forms about 90:10 to about 60:40.

Dried products, for example foams or powders, that incorporate the fibrin hydrolysate material, alone or in combination with one or more additional matrix-forming substances (including for example a dialdehyde starch or a dialdehyde starch hydrolysate material as described herein), can be characterized by their water sorption capacity. In certain forms, such a dried product exhibits a capacity to absorb at least 10 times its weight, or at least 20 times it weight, considered on a dry weight basis, of water at pH 7 at 20° C. In especially preferred forms, a dried foam, powder or other product incorporating the fibrin hydrolysate will exhibit a capacity to absorb about 10 to about 80 times its weight in water, more typically about 15 to about 60 times its weight in water, at a pH of 7 and temperature of 20° C.

Dried foams that incorporate the fibrin hydrolysate material, alone or in combination with one or more additional substances, can in some embodiments have a specific density (mass/volume) of about 0.1 g/cm$^3$ or less, and in certain forms in the range of about 0.01 g/cm$^3$ to about 0.1 g/cm$^3$ or in the range of about 0.02 g/cm$^3$ to about 0.07 g/cm$^3$.

The inclusion of other matrix-forming materials or other substances along with the fibrin hydrolysate material can impact the water sorption capacity and/or specific density of a powder, foam or other product, but the selection of materials and their levels for incorporation can be controlled to result in products having the water absorption capacities and/or specific densities identified herein. As well, the inclusion of other matrix-forming materials along with the fibrin hydrolysate material can impact the physical handling properties of the product, for example in the case of foam bodies where the inclusion of another matrix-forming material along with the fibrin hydrolysate material can decrease the friability of the foam body when dry and/or enhance the integrity of the foam body when wetted.

In addition to or as an alternative to the combination of the fibrin hydrolysate material with other matrix-forming materials, the fibrin hydrolysate material can be combined with other components, including for example bioactive components. These may include, for example, added growth factors, cytokines, clotting factors, drugs, clotting promoters, and/or other added substances useful in a given end use of the product.

In addition to its incorporation into dried products, a fibrin hydrolysate material as described herein can be incorporated into wet products, typically including an aqueous liquid medium. For example, the fibrin hydrolysate material, alone or in combination with one or more other substances, including any of those identified herein, can be incorporated in a gel product (e.g. packaged in a syringe or other container from which it can be dispensed onto or into a site of bleeding). When gels are provided, they will typically have viscosity of greater than 1 centipoise, and in certain embodiments at least about 5000 centipoise.

The foam, powder or other product (for example an aqueous gel or suspension) incorporating the fibrin hydrolysate material can, in certain embodiments, be useful in promoting hemostasis, for example at a bleeding site in a human or other animal patient. In regard to applications where use in promoting hemostasis will be beneficial, these include general surgery or biopsy surgery techniques that create a site of bleeding, e.g. biopsy or other surgery on parenchymatous organs (liver, kidney, spleen etc.), cardiovascular surgery, thorax surgery, grafting surgery, orthopedic surgery, surgical operations in the fields of bone surgery and plastic surgery, ear, nose and throat surgery, operations in the field of neurosurgery, operations in the urologic and gynecologic tracts, as well as generally for hemostasis as well as for treating wounds.

In preferred forms, the product incorporating the fibrin hydrolysate material will exhibit substantial capacity to promote clotting of blood, including human blood. The active hemostatic properties of the preferred fibrin hydrolysate material or product incorporating the fibrin hydrolysate material can be resultant of the inclusion of residual components of the fibrin-containing gel starting material and/or from the inclusion of components formed during the hydrolysis processing. These components which cause active promotion of hemostasis may for example include the presence of fibrin monomers, thrombin, or other components involved in the blood clotting cascade.

In addition to uses in promoting hemostasis, products incorporating the fibrin hydrolysate may also be used in other applications where implantation or other administration of the fibrin hydrolysate material or product incorporating it may be beneficial. For example, a foam body of or incorporating the fibrin hydrolysate material may be used in applications where it is desired to plug, occlude, or fill openings, cavities, or passages in a human or other animal patient. As one example, powders or foams containing the fibrin hydrolysate material may be used in vascular occlusion, to occlude blood vessels such as arteries or veins in a human or other animal patient. The foam, powder or other product incorporating the fibrin hydrolysate material may also be used in other applications, including for example as a cell growth substrate or support material for in vitro cell culture.

In other aspects disclosed herein, hemostatic or other products incorporate a dialdehyde starch hydrolysate material. A dialdehyde starch hydrolysate material can be prepared by subjecting a dialdehyde starch to hydrolysis conditions. The dialdehyde starch can be prepared using known techniques in which a starch is oxidized, typically in the presence of periodate, or can be obtained from commercial sources. A dialdehyde starches with at least a 50% dialdehyde content (i.e. at least 50% of the original sugar rings in the starch starting material have been converted to dialedhyde containing groups) can be used. In some embodiments, a dialdehyde starch with a 50% to 100% dialdehyde content is used, more preferably a 70% to 100% dialdehyde content. In certain embodiments, the dialdehyde starch starting material will have an 80% to 100%, or 90% to 100%, dialdehyde content.

The hydrolysis conditions used to prepare the dialdehyde starch hydrolysate will be controlled to achieve a partial hydrolysis of the starting dialdehyde starch material so as to result in a water-insoluble, water-swellable dialdehyde starch hydrolysate product. The hydrolysis conditions can be in acidic aqueous medium (pH below 7), neutral aqueous medium (pH of 7), or in basic aqueous medium (pH above 7), or combinations thereof. Hydrolysis of the dialdehyde starch in an acidic aqueous medium is preferred, more preferably in an acidic aqueous medium having a pH below about 5, or even more preferably a pH of about 4 or lower, is preferred. Common examples of acids that can be used include, but are not limited to, strong acids, i.e., acids that completely dissociate in aqueous solution such as, but not limited to hydrochloric acid (HCl), sulfuric acid ($H_2SO_4$), phosphoric acid ($H_3PO_4$), weak acids and/or organic acids including, but not limited to carboxylic acids such as acetic acid (HOAc).

The temperature of the hydrolysis conditions will also impact the progress of the hydrolysis of the dialdehyde starch. A liquid hydrolysis medium contacted with a dialdehyde starch at a temperature in the range of about 1° C. to about 100° C., more preferably in the range of about 50° C. to about 95° C., is preferred. In addition or alternatively, the time period over which the starting dialdehyde starch material is contacted with a hydrolysis medium can be used to control the extent of hydrolysis. In preferred dialedhyde starch hydrolysis processes, the dialdehyde starch is contacted with the hydrolysis medium for a period of time in the range of about 3 minutes to about 10 hours, or about 5 minutes to about 2 hours, or about 10 minutes to about 90 minutes. It will be understood, however, that other times and temperatures may be used in broader aspects of the present disclosure, and that these and other conditions affecting the rate of hydrolysis can be controlled to provide dialdehyde starch hydrolysate materials with the properties discussed herein.

In this regard, as discussed above, the hydrolysis process is controlled so as to result in a dialdehyde starch hydrolysate that is water-insoluble but water-swellable. The hydrolysis processing will also preferably be conducted so as to yield a substantial percentage by weight of the starting dialdehyde starch material as a water-insoluble, water-swellable dialdehyde starch hydrolysate material. For example, the hydrolysis process can yield at least 50 percent by weight of the starting dialdehyde starch material as a water-insoluble, water-swellable diadehyde starch hydrolysate material, more preferably at least 60 percent, and even more preferably at least 70 percent. In particularly preferred processes, at least 80 percent by weight of the starting dialdehyde starch material will be yielded as the water-insoluble, water-swellable dialdehyde starch product. The hydrolysis process is controlled to achieve such yield. If the hydrolysis processing conditions are too harsh and/or too long, too much or all of the starting dialdehyde starch material will be rendered soluble, thereby disrupting or reducing the desired gel-forming capacities and other potential properties of the controlled dialdehyde starch hydrolysate material discussed herein.

The hydrolysis process can be terminated in any suitable fashion. For example, where heating is used to promote the hydrolysis of the dialdehyde starch, the hydrolysis medium can be cooled to slow or essentially terminate the hydrolysis process.

During the hydrolysis process, the starting dialdehyde starch particles and forming or formed dialdehyde starch hydrolysate can swell relative to the starting dialdehyde starch particles. For example, the volume of the formed water-insoluble but water swellable dialdehyde starch hydrolysate can be at least two times, at least three times, at least four times, or at least five times that of the starting dialdehyde starch, and typically not more than ten times that of the starting dialdehyde starch. The pH of the hydrolysis medium, the duration of the hydrolysis, and/or the temperature can be controlled to provide these levels of increase in the volume of the starting dialdehyde starch particles.

In addition or alternatively, the hydrolysis process can change the physical and/or chemical properties of the dialdehyde starch. For example, as compared to the starting dialdehyde starch material, the dialdehyde starch hydrolysate may have one, some or all of the following features:

a lower weight average molecular weight ($M_w$), in some forms at least 2% lower; and/or a higher amount of carboxylic acid (—COOH) groups (formed by conversion of some of the aldehyde groups (—HC=O) of the dialdehyde starch (see formula for repeating dialdehyde groups given above) to carboxylic acid groups (—COOH); and/or a lower amount of aldehyde (—HC=O) groups; and/or an increased dispersibility in deionized water, for example as measured by Song et al., Starch 2010, 62, 458-486; and/or a decreased particle size in suspension in water, for example as measured by light scattering as described in Song et al., Starch 2010, 62, 458-486.

The dialdehyde starch hydrolysate material can be used immediately in the preparation of further products, for example hemostatic products, or can be stored wet or dry (e.g. lyophilized form) prior to further use. The dialdehyde starch hydrolysate suspension from the hydrolysis process can be used as a whole, with or without adjustment of pH (e.g. the dialdehyde starch hydrolysate can be acidic, neutral or basic, preferably acidic, when processed to form products as described herein), or the dialdehyde starch hydrolysate can be recovered from the suspension, potentially washed, and then stored or used. The dialdehyde starch hydrolysate material may also be modified for incorporation into products. For example, it may be subjected to shearing forces, for example by blending with a rotating blade blender, to shear the material and/or aerate the material, before its use in downstream processing. In certain aspects the dialdehyde starch hydrolysate in a hydrated, swollen condition (e.g. appearing as a gel phase) is sheared and aerated to prepare an aerated gel, which can be used in or as a gel product or which can be incorporated as or in a castable preparation that is charged to a mold and dried, e.g. by lyophilization, to form a foam body. The foam body may, for example, be in the form of a sheet, block or cylinder.

The dialdehyde starch hydrolysate material can be used in any suitable amount or fashion in the preparation of products. In certain forms, the dialdehyde starch hydrolysate material will be used in the preparation of formed bodies (e.g. foams) or powders that contain the dialdehyde starch hydrolysate material, or in the preparation of gels. Such bodies, powders or gels, or other products, can be constituted entirely of the dialdehyde starch hydrolysate material or can include the dialdehyde starch hydrolysate material in combination, such as in admixture, with one or more other materials. In certain embodiments, the dialdehyde starch hydrolysate material is incorporated in a formed body or other product in combination with a matrix-forming material other than the dialdehyde starch hydrolysate material. Such a matrix-forming material can include for example one or more natural and/or synthetic polymers. As natural polymers candidates include collagen, gelatin, fibrin, a fibrin hydrolysate material as described herein, and other matrix-forming materials prepared synthetically or derived from tissues of plants or animals. In preferred forms, the natural or synthetic polymer or polymers included with the dialdehyde starch hydrolysate material will be biocompatible and/or bioabsorbable. In certain forms, the dialdehyde starch hydrolysate material is incorporated in a formed body such as a foam body along with a matrix-forming natural or synthetic polymeric material, with such matrix-forming polymeric material in some variants of the invention being an expanded collagenous extracellular matrix (ECM) or other collagen-containing material. The expanded collagenous ECM or other collagen-containing material can be prepared, for example, as described in U.S. Patent Application Publication No. 20090326577 of Cook Biotech Incorporated, published Dec. 31, 2009, which is hereby incorporated herein by reference. In such preparation, the ECM or other collagen-containing material can be formed by contact with a basic liquid medium under conditions and for a period of time effective to expand the starting collagen-containing tissue material to provide the expanded material, e.g. with the expanded collagen-containing tissue material having a volume that is at least 150% of that of the starting ECM or other collagen-containing tissue material. Expanded submucosal ECM materials are preferred for these purposes. When any of these or another matrix-forming material other than the fibrin hydrolysate material is used, it can be used in a dry weight ratio of about 90:10 to about 10:90 relative to the fibrin hydrolysate material, more preferably about 70:30 to about 30:70, and in certain forms about 90:10 to about 60:40.

Dried products, for example foams or powders, that incorporate the dialdehyde starch hydrolysate material, alone or in combination with one or more additional matrix-forming substances (for example in combination with a fibrin hydrolysate material as described herein), can be characterized by their water sorption capacity. In certain forms, such a dried product exhibits a capacity to absorb at least 2 times its weight, or at least 5 times it weight, considered on a dry weight basis, of water at pH 7 at 20° C. In preferred forms, a dried foam, powder or other product incorporating the dialdehyde starch hydrolysate will exhibit a capacity to absorb about 2 to about 80 times its weight in water, or about 5 to about 50 times its weight in water, at a pH of 7 and temperature of 20° C.

Dried foams that incorporate the dialdehyde starch hydrolysate material, alone or in combination with one or more additional substances, can in some embodiments have a specific density (mass/volume) of about 0.1 $g/cm^3$ or less, and in certain forms in the range of about 0.01 $g/cm^3$ to about 0.1 $g/cm^3$ or in the range of about 0.02 $g/cm^3$ to about 0.07 $g/cm^3$.

The inclusion of other matrix-forming materials or other substances along with the dialdehyde starch hydrolysate material can impact the water sorption capacity and/or specific density of a powder, foam or other product, but the selection of materials and their levels for incorporation can be controlled to result in products having the water absorption capacities and/or specific densities identified herein. As well, the inclusion of other matrix-forming materials along with the dialdehyde starch hydrolysate material can impact the physical handling properties of the product, for example in the case of foam bodies where the inclusion of another matrix-forming material along with the dialdehyde starch hydrolysate material can decrease the friability of the foam body when dry and/or enhance the integrity of the foam body when wetted.

In addition to or as an alternative to the combination of the dialdehyde starch hydrolysate material with other matrix-forming materials, the dialdehyde starch hydrolysate material can be combined with other components, including for example bioactive components. These may include, for example, added growth factors, cytokines, clotting factors, drugs, clotting promoters, and/or other added substances useful in a given end use of the product.

In addition to its incorporation into dried products, a dialdehyde starch hydrolysate material as described herein can be incorporated into wet products, typically including an aqueous liquid medium. For example, the dialdehyde starch hydrolysate material, alone or in combination with one or more other substances, including any of those identified herein, can be incorporated in a gel product (e.g. packaged in a syringe or other container from which it can be dispensed onto or into a site of bleeding). When gels are provided, they will typically have viscosity of greater than 1 centipoise, and in certain embodiments at least about 5000 centipoise.

The foam, powder or other product (for example an aqueous gel or suspension) incorporating the dialdehyde starch hydrolysate material can, in certain embodiments, be useful in promoting hemostasis, for example at a bleeding site in a human or other animal patient. In regard to applications where use in promoting hemostasis will be beneficial, these include general surgery or biopsy surgery techniques that create a site of bleeding, e.g. biopsy or other surgery on parenchymatous organs (liver, kidney, spleen etc.), cardiovascular surgery, thorax surgery, grafting surgery, orthopedic surgery, surgical operations in the fields of bone surgery and plastic surgery, ear, nose and throat surgery, operations in the field of neurosurgery, operations in the urologic and gynecologic tracts, as well as generally for hemostasis as well as for treating wounds.

In preferred forms, the product incorporating the dialdehyde starch hydrolysate material will exhibit substantial capacity to promote clotting of blood, including human blood. The hemostatic properties of the preferred dialdehyde starch hydrolysate material or product incorporating the dialdehyde starch hydrolysate material can be resultant of the dialdehyde starch hydrolysate material itself and/or of the inclusion of other components (e.g. fibrin hydrolysate as described herein, fibrinogen, fibrin monomers and/or thrombin) which cause active promotion of hemostasis.

In addition to uses in promoting hemostasis, products incorporating the dialdehyde starch hydrolysate may also be used in other applications where implantation or other administration of the dialdehyde starch hydrolysate material or product incorporating it may be beneficial. For example, a foam body of or incorporating the dialdehyde starch hydrolysate material may be used in applications where it is desired to plug, occlude, or fill openings, cavities, or passages in a human or other animal patient. As one example, powders or foams containing the dialdehyde starch hydrolysate material may be used in vascular occlusion, to occlude blood vessels such as arteries or veins in a human or other animal patient.

In certain aspects, hemostatic or other products herein include both a fibrin hydrolysate material, e.g. having any of those properties described herein for a fibrin hydrolysate material, and a dialdehyde starch or a dialdehyde starch hydrolysate material as described herein, e.g. having any of those properties described herein for a dialdehyde starch or dialdehyde starch hydrolysate material. When used together in a hemostatic or other product, the fibrin hydrolysate material and the dialdehyde starch or dialdehyde starch hydrolysate material can be used in a weight ratio, on a dry weight basis, of about 1:99 to about 99:1, more preferably about 10:90 to about 90:10, and even more preferably about 30:70 to about 70:30. In certain embodiments, the fibrin hydrolysate material is used in an amount, on a weight basis, that is greater than that of the dialdehyde starch or dialdehyde starch hydrolysate material. The hemostatic or other product can be in any of those physical forms described herein, including for example as an aqueous preparation such as a suspension or gel, or as a dry product such as a powder or foam. In cast foams or other cast products, the dialdehyde starch or dialdehyde starch hydrolysates can, in some embodiments, serve as a chemical crosslinker to introduce covalent intermolecular crosslinks within the fibrin hydrolysate material. For these purposes, aldehyde groups of the dialdehyde starch or dialdehyde starch hydrolysate can react with amino groups of the amino acids of the fibrin hydrolysate material. Similarly, where the dialdehyde starch hydrolysate is used in combination with one or more matrix-forming protein materials other than fibrin hydrolysate materials (e.g. collagen or collagen-containing materials, or other matrix-forming protein materials described herein), it can serve as a chemical crosslinker to introduce intermolecular covalent crosslinks within the matrix-forming protein materials.

For medical or other uses, the fibrin hydrolysate material or products incorporating it, or the dialdehyde starch hydrolysate material or products incorporating it, can be provided in a package in sterile condition. This may be achieved by any suitable technique. In certain modes the fibrin hydrolysate material or product including it, or the dialdehyde starch material or product including it, is sealed in a package, and the package is then subjected to terminal sterilization, for example, by irradiation, ethylene oxide gas, or any other suitable terminal sterilization technique. In other modes the fibrin hydrolysate material or product incorporating it, or the dialdehyde starch material or product incorporating it, will be prepared and packaged under sterile conditions, such that no terminal sterilization is needed. These and other modes of providing a sterile packaged product known to those practiced in the field can be used.

In order to promote a further understanding of the present invention and its various embodiments, the following specific examples are provided. It will be understood that these examples are illustrative and not limiting of the invention.

EXAMPLE 1

Preparation of Fibrin Clot Material from Platelet Concentrate

Disease-screened apheresed human platelet units (obtained from peripheral blood) that have just expired after a 5-day shelf life are collected and frozen at −20° C. in a freezer until use. A number of the units (e.g. about 10 or more units) are removed from the freezer and thawed at room temperature, thus lysing the platelets. The platelet lysate preparation from the units is pooled into a bag. Calcium chloride is added to the pooled platelet lysate at a level of 0.75 grams/L and then thoroughly mixed with the lysate on a shaker at room temperature for 2 hours. After mixing, the $CaCl_2$-treated platelet lysate is allowed to clot overnight at room temperature, during which a firm, substantially homogeneous clotted material forms. While remaining closed, the bag containing the clotted material is pressed to express liquid from the gel clot. This pressing is thoroughly done, resulting in a solid clot material at one end of the bag and a separate liquid volume at the other end of the bag, adjacent an outlet spout. The separated liquid represents approximately 75-80% of the volume of the original, pooled platelet lysate, and the solid clot material represents the remainder. The liquid is transferred from the bag to a second bag and can optionally be used as or in the manufacture of a platelet lysate liquid useful, for example, in cell culture or as a therapeutic substance. The clotted solids material, rich in fibrin and also containing other components from the pooled lysate, can be used immediately, or after storage (e.g. in a lyophilized, refrigerated or frozen condition) in the manufacture of fibrin hydrolysate compositions as described herein.

EXAMPLE 2

Preparation of Fibrin Hydrolysate Materials

A water-insoluble but water-swellable fibrin hydrolysate ("F-H") material was prepared as follows. A clotted solids material prepared as in Example 1 and having a soft gel consistency was combined with one molar (1 M) sodium hydroxide (NaOH) in a 1:2.5 weight to volume ratio (w/v). The resulting mixture was placed in a refrigerator at about 4° C. for one hour for controlled hydrolysis of the fibrin material to form a water-swellable fibrin hydrolysate material. The mixture was then removed from the refrigerator, and the liquid fraction decanted from the water-insoluble fibrin hydrolysate fraction. High purity water was added to the fibrin hydrolysate fraction, and the resulting mixture was shaken on an orbital shaker for about 10 minutes at room temperature to rinse the solid. The liquid fraction was then decanted from the insoluble fraction. The insoluble fraction was washed again with high purity water, and then with 0.2 molar (0.2 M) acetic acid, and then again with water five times according to the above procedure (10 minutes on shaker for each wash at room temperature, followed by decanting the rinse water). After the fifth rinse on the shaker with high purity water, the solid fibrin hydrolysate material was allowed to incubate in the high purity water at room temperature for an additional hour to swell the fibrin hydrolysate material. The excess water was then drained off and the pH of the drained rinse water was measured to confirm that the pH was substantially neutral. The drained, water-swollen fibrin hydrolysate was then blended at high speed in a blender to form a fine gel. The composition can be used at this stage as a flowable aqueous fibrin hydrolysate gel, or treated further to form a dried fibrin hydrolysate foam. To obtain a dried foam body, the gel was casted into molds of the desired shape (cylindrical for these runs) and then lyophilized for three days.

EXAMPLE 3

Preparation of Collagenous ECM Hydrolysate Materials

A water-insoluble but water-swellable collagenous ECM hydrolysate ("ECM-H") material was prepared as follows. Small intestine submucosa (SIS) obtained from Cook Biotech Incorporated (Lafayette, Ind.) was combined with 2.25 molar (2.25 M) sodium hydroxide (NaOH) in a 1:10 wt/vol ratio. The resulting mixture was placed in a refrigerator at about 4° C. for one hour. The mixture was then removed from the refrigerator, and the liquid fraction decanted from a solid fraction. High purity water was added to the solid fraction, and the resulting mixture was shaken on an orbital shaker for about 10 minutes at room temperature to rinse the solid. After shaking for about 10 minutes, the liquid fraction was decanted from the solid fraction. The solid fraction was washed again with water, then with 0.2 molar (0.2 M) acetic acid, then with water five times according to the above procedure (10 minutes on shaker for each wash at room temperature, followed by decanting the rinse water). The pH of the last rinse was measured to confirm that it was substantially neutral. The drained ECM hydrolysate solids were combined with high purity water (1:1 wt/vol) and then blended at high speed in a blender to form a fine gel. The gel was poured into molds and casted into the desired shape (cylindrical in these runs) and then lyophilized to obtain dried foam bodies.

EXAMPLE 4

Preparation of Combined Fibrin/ECM Hydrolysate Materials

Drained fibrin hydrolysate material prepared as in the Example 2 and drained ECM hydrolysate material prepared as in Example 3 were combined in a 50:50 or 40:60 wt/wt ratio and then blended at high speed in a blender to form a fine gel. The gel was poured into molds and casted into the desired shape (cylindrical in these runs) and then lyophilized to obtain dried foam bodies.

EXAMPLE 5

In Vivo Hemostasis Testing in Acute Porcine Model

Materials and Methods:

Two domestic pigs were placed under general anesthesia. Blood samples were obtained to test for the prothrombin time ("PT"), partial thromboplastin time ("PTT"), and activated clotting time ("ACT") for each pig via standard laboratory blood tests.

The abdominal cavity was exposed with a midline incision, and a 14-gauge 5-mm deep biopsy punch was used to wound certain organs and initiate blood flow. For each pig, the spleen, live, and kidneys were tested.

For Pig 1, the order or organs tested was spleen, liver, and then left kidney. For Pig 2, the order of organs tested was liver, left kidney, and then spleen.

For each organ, a biopsy punch was used to create a wound. As blood started to flow, gauze was used to clog the wound, and the test composition was applied to the wound. For control, a wound was formed with a biopsy punch and allowed to bleed freely, with no composition applied. Compositions of Example 2, 3 or 4 were tested in each organ of each pig. Certain dried foam compositions were applied without hydration, while some were applied after hydration with phosphate buffered saline (PBS). For some wounds, if the blood flow from a wound caused the test material to become forced out of the wound, light pressure by hand was used to prevent the material from being force out of the wound. For gel trials about 1 to 1.5 mL was initially applied, and in some trials re-applications were made during the test to counteract wash-out of prior applied material by blood flow. Additionally, after an initial trial of the ECM-H gel in the Pig 1 spleen exhibited no signs of hemostasis after 23 minutes, no further testing of the ECM-H gel was conducted.

Primary hemostasis was observed by lightly blotting around a wound to check for the appearance of wet or liquid blood. This change of wet or liquid blood to a gel state was measured and recorded as the time to hemostasis for each wound.

At a maximum of three hours after anesthesia, each pig was euthanized.

Results:

Table 1 summarizes the observed time to hemostasis for Pig 1 and Pig 2 in spleen.

TABLE 1

Observed time to hemostasis in porcine spleen.

| | Time to hemostasis in spleen (mm:ss) | |
|---|---|---|
| Composition | Pig 1 | Pig 2 |
| Example 2 (F-H foam) | 12:24 (PBS-hydrated foam) | 00:22 (dry foam) |
| Example 3 (ECM-H foam) | 17:24 (dry foam) | 14:43 (dry foam) |
| Example 4 (F-H/ECM-H foam, 50:50) | 16:55 (PBS-hydrated foam) | 03:02 (dry foam) |

TABLE 1-continued

Observed time to hemostasis in porcine spleen.

| | Time to hemostasis in spleen (mm:ss) | |
|---|---|---|
| Composition | Pig 1 | Pig 2 |
| Example 2 (F-H gel) | 21:49 (re-applications at 1 and 6 min.) | 07:33 |
| Control | >36:38 | >30:00 |

Table 2 summarizes the observed time to hemostasis for Pig 1 and Pig 2 in liver.

TABLE 2

Observed time to hemostasis in porcine liver.

| | Time to hemostasis in liver (mm:ss) | |
|---|---|---|
| Composition | Pig 1 | Pig 2 |
| Example 2 (F-H foam) | 03:54 (PBS-hydrated foam) | 03:15 (dry foam) |
| Example 3 (ECM-H foam) | 15:06 (dry foam) | 11:18 (dry foam) |
| Example 4 (F-H/ECM-H foam, 50:50) | 07:04 (PBS-hydrated foam) | 02:17 (dry foam) |
| Example 2 (F-H gel) | 19:37 (re-application at 4 min.) | 29:12 (re-application at 2 min.) |
| Control | >30:00 | >27:00 |

Table 3 summarizes the observed time to hemostasis for Pig 1 and Pig 2 in kidney.

TABLE 3

Observed time to hemostasis for porcine kidney.

| | Time to hemostasis in kidney (mm:ss) | |
|---|---|---|
| Composition | Pig 1 | Pig 2 |
| Example 2 (F-H foam) | 03:54 (dry foam) | 01:43 (dry foam applied; PBS drip applied soon after) |
| Example 3 (ECM-H foam) | 07:17 (dry foam) | 09:50 (dry foam) |
| Example 4 (F-H/ECM-H foam, 50:50) | 03:24 (dry foam) | 01:10 (dry foam) |
| Example 2 (F-H gel) | 05:19 | 06:35 |
| Control | 07:16 | 06:59 |

Table 4 summarizes the baseline PT, PTT, and ACT values that were determined by routine laboratory tests for Pig 1 and Pig 2.

TABLE 4

Summary of PT, PTT, and ACT values for Pig 1 and Pig 2 (in seconds).

| Baseline Test | Pig 1 | Pig 2 |
|---|---|---|
| PT | 19.0 s | 18.0 s |
| PTT | 74.0 s | 72.0 s |
| ACT | 110 s | 102 s |

General Observations. The dried foam compositions of Example 4 (blended F-H/ECM-H foams) had a consistency that was spongier than the dried foam compositions of Example 2 (F-H only foams), with the latter tending to crumble to a powder when compressed rather than remaining intact as a unitary solid body. The dried foam compositions of Example 4 also demonstrated an enhanced capacity to absorb blood relative to those of Example 2, while retaining an ability to initiate hemostasis. In this sense, the Example 4 foams were able to advantageously act as both passive and active hemostasis promoters.

EXAMPLE 6

Measurement of Water Sorption Capacity of Dried Foams

Dried foams comprising F-H, ECM-H, and combinations thereof were prepared as described in Examples 2, 3 and 4. The water absorption capacities of these dried materials were measured at room temperature using high purity water. The average water sorption capacity for F-H foam samples was about 42 times dry weight, for ECM-H foam samples was about 9 times dry weight, and for F-H:ECM-H (40:60) foam samples was about 19 times dry weight.

EXAMPLE 7

In Vivo Hemostasis Testing in Acute Porcine Model

Figure 1:
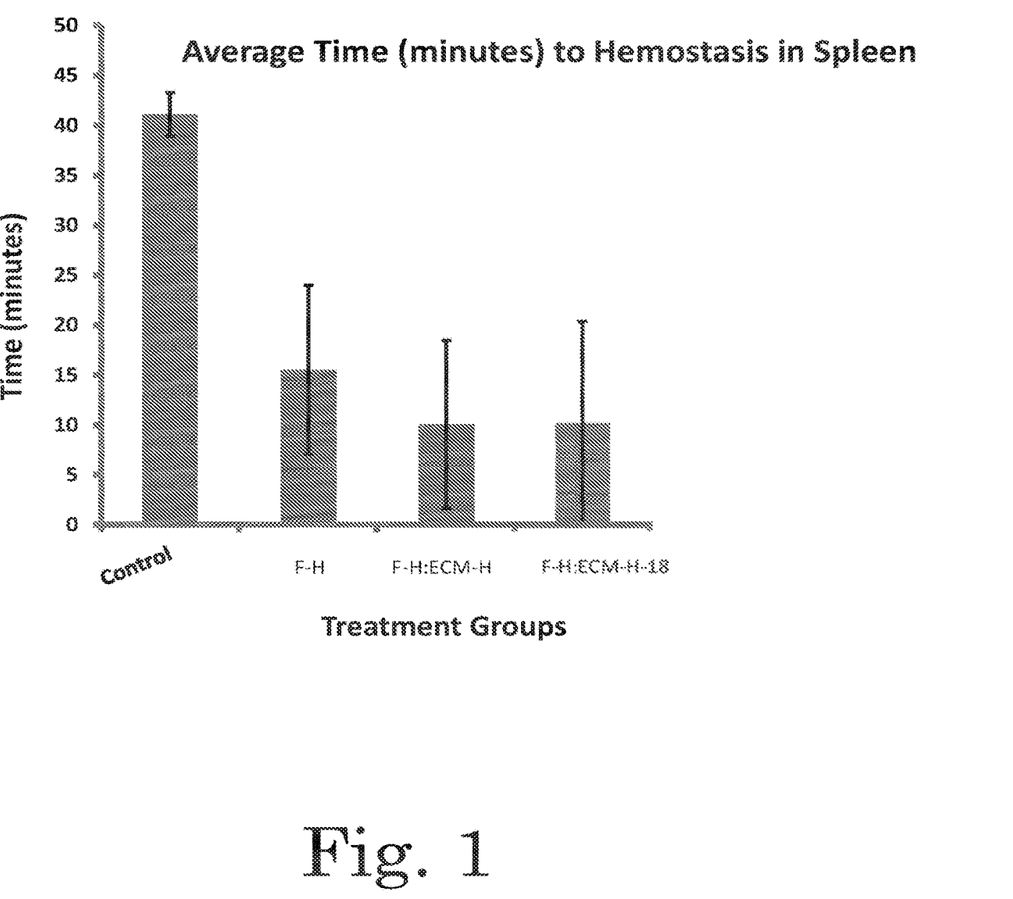
FIG. 1 shows a graphical representation of the average time in minutes to hemostasis in porcine spleen, as described further in Example 7 below.
Figure 2:
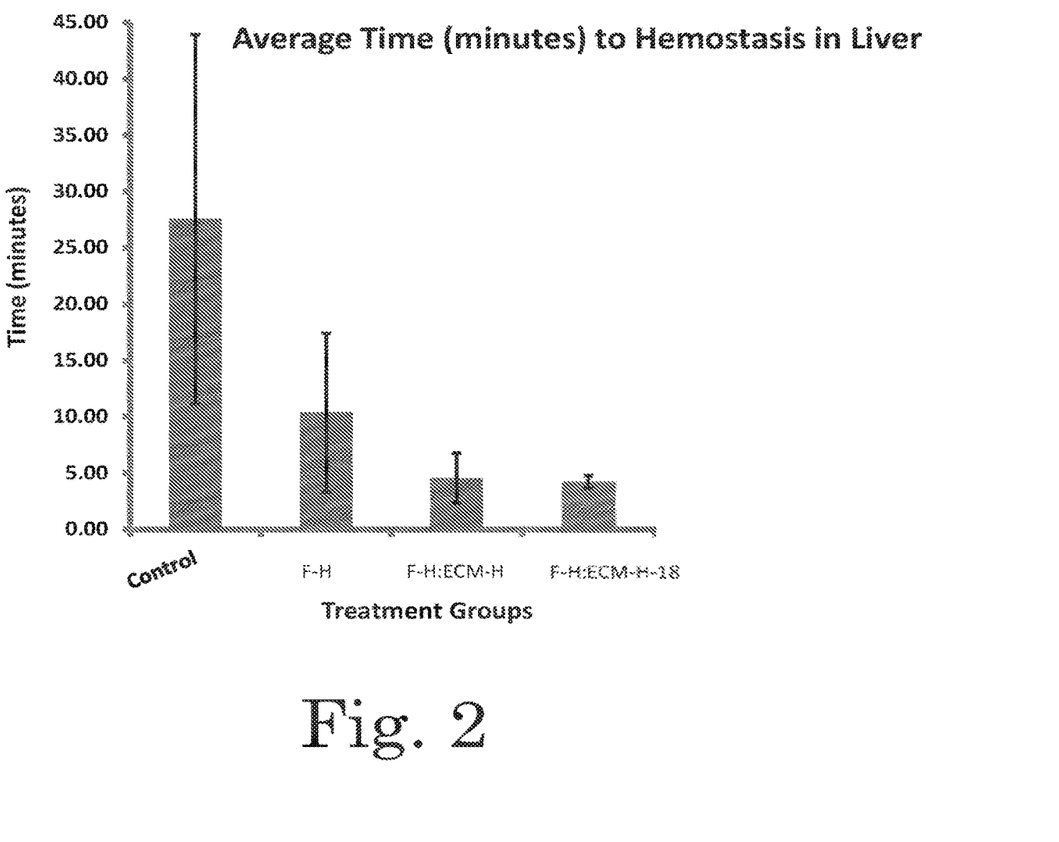
FIG. 2 shows a graphical representation of the average time in minutes to hemostasis in porcine liver, as described further in Example 7 below.
Figure 3:
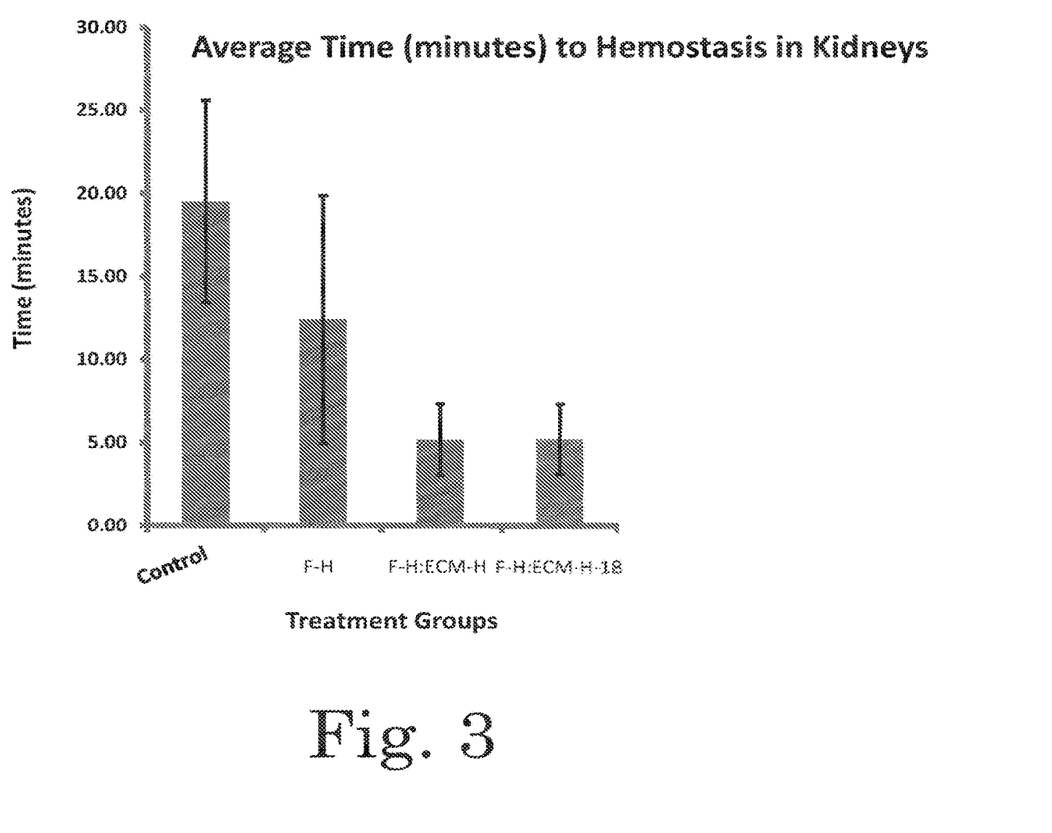
FIG. 3 shows a graphical representation of the average time in minutes to hemostasis in porcine kidneys, as described further in Example 7 below.

Dried foams prepared as described in Examples 2, 3 and 4 were subjected to additional in vivo testing, generally as described in Example 5 above. The foams were a F-H only foam, a combined F-H:ECM-H foam (40:60) prepared as in Example 4, and a combined F-H:ECM-H foam (40:60) foam prepared as in Example 4, except that the F-H was allowed to incubate for 18 hours at room temperature (instead of one hour as in Example 2) to allow additional swelling prior to further use to prepare the combined F-H:ECM-H foam (designated "F-H:ECM-H-18). The results are summarized in FIGS. 1 to 3 and show that the F-H and F-H:ECM-H foams effectively promote hemostasis relative to the control (gauze).

EXAMPLE 8

Preparation of Dialdehyde Starch Hydrolysate Material

High dialdehyde content (96.12%) starch from Monomer-Polymer and Dajac Labs was heated at 80° C. in either hydrochloric acid (HCl) or high purity water (HPW) for various time points, dependent on visual observation of the swelling of the starch until it was about 5 times larger than the starting material. A 10% w/v (starch to solution) was used during the hydrolysis of the starch. Concentrations of HCl of 0.1 N or 0.01 N were used (resulting in products designated DAS(0.1 N) and DAS(0.01 N) respectively) and in some HCl runs the pH was monitored every half hour and adjusted from a pH of 1 to a pH of 4 using 5M sodium hydroxide (NaOH) solution (resulting in a product designated DAS(pH 4). The HPW reaction resulted in a product designated DAS(HPW). All samples were stirred using an overhead stirrer at 180 rpm to allow for constant stirring while the starch was being heated. The result was a modified dialdehyde starch material substantially swollen relative to the starting dialdehyde starch material.

EXAMPLE 9

Preparation of Dialdehyde Starch Foam Materials

Finished dialdehyde starch hydrolysate suspensions prepared as in Example 8 (used as a whole without pH adjustment) alone, or combined with drained fibrin hydrolysate (F-H) material prepared as in the Example 2 in a 40:60 wt/wt ratio, was blended at high speed in a blender to form a fine gel. The gel was poured into molds and cast into the desired shape (cylindrical in these runs, 3.5 cm in diameter) and then lyophilized to obtain dried foam bodies. The foam products that were prepared are summarized in Table 5 below:

TABLE 5

Summary of Prepared DAS Hydrolysate Foams

| Composition | Components |
| --- | --- |
| 9A | DAS(0.1N):F-H |
| 9B | DAS(HPW):F-H |
| 9C | DAS(0.01N):F-H |
| 9D | DAS(pH 4):F-H |
| 9E | DAS(pH 4) |

EXAMPLE 10

In Vivo Hemostasis Testing in Acute Porcine Model

Dried foam compositions prepared as described in Example 9 and summarized in Table 5 were subjected to in vivo hemostasis testing in the liver and spleen, generally as described in Example 5 above. In these experiments, pressure was applied to each composition for 1 minute immediately after application. The degree of bleeding from each wound was then evaluated after the 1 minute hold and at 2 and 5 minutes. In some tests the foam cylinders were placed overtop the punch wounds site and in others they were broken into pieces (one-quarter to one-half the original 3.5 cm cylinder size) and inserted into the punch wounds. All of the compositions were able to be applied as foams and did not crumble into powder, and they successfully absorbed blood and had hemostatic effect. Compositions 9A, 9D and 9E successfully provided immediate hemostasis (following the initial 1 minute hold), performing better than compositions 9B and 9C which did not provide immediate hemostasis under the conditions tested. These relative capacities to initiate hemostasis generally coincided with the results of in vitro blood clotting time testing for these same compositions.

Listing of Certain Disclosed Embodiments

The following provides a non-limiting, enumerated listing of some of the embodiments disclosed herein.

Embodiment 1

A method for making a hemostasis promoting material, comprising:
subjecting a fibrin-containing starting material to hydrolysis conditions so as to form a fibrin hydrolysate material having an increased sorption capacity, relative to the fibrin starting material, for water at a pH of 7.

Embodiment 2

The method according to Embodiment 1, wherein the hydrolysis conditions comprise contacting the fibrin starting material with a basic liquid medium and/or wherein the fibrin hydrolysate material exhibits a sorption capacity for water at a pH of 7 and a temperature of 20° C. of at least about 10 times its dry weight.

Embodiment 3

The method according to Embodiment 1 or 2, wherein the basic liquid medium has a pH in the range of about 10 to 14 and/or wherein the basic liquid medium comprises sodium hydroxide or potassium hydroxide.

Embodiment 4

The method of Embodiment 3, wherein the basic liquid medium comprises sodium hydroxide.

Embodiment 5

The method of any one of the preceding Embodiments, also comprising lyophilizing the fibrin hydrolysate material.

Embodiment 6

The method of any one of the preceding Embodiments, also comprising combining the fibrin hydrolysate material with at least one additional matrix forming material.

Embodiment 7

The method of any one of the preceding Embodiments, wherein the subjecting is for a period of time of at least about 10 minutes, more preferably wherein the period of time is about 20 minutes to about 2 hours.

Embodiment 8

The method of any one of the preceding Embodiments, wherein the subjecting is conducted at a temperature in the range of about 0° C. to about 15° C.

Embodiment 9

The method of any one of the preceding Embodiments, also comprising casting a castable preparation containing the fibrin hydrolysate material, and drying the castable preparation to form a solid body.

Embodiment 10

The method of Embodiment 9, wherein the castable preparation is free from added chemical crosslinkers.

Embodiment 11

The method of Embodiment 9 or 10, also comprising sterilizing the solid body to form a sterile solid body, and preferably wherein the sterilizing is conducted on the solid body without the solid body having been chemically cross-linked prior to the sterilizing.

Embodiment 12

The method of any one of the preceding Embodiments, wherein the fibrin hydrolysate material is thrombin-reactive and/or calcium-reactive.

Embodiment 13

The method of any one of the preceding Embodiments, wherein the starting fibrin-containing material is a clot material, more preferably a calcium-initiated clot material.

Embodiment 14

The method of Embodiment 13, wherein the clot material has been formed by clotting a lysed platelet composition.

Embodiment 15

The method of Embodiment 14, wherein the lysed platelet composition has been formed by lysing a platelet concentrate, the platelet concentrate having a platelet concentration of about $10^5$ platelets per ml or greater.

Embodiment 16

The method of Embodiment 14, wherein the lysed platelet composition has been formed by lysing a platelet concentrate, the platelet concentrate having a platelet concentration of about $10^7$ platelets per ml or greater.

Embodiment 17

The method of Embodiment 14, wherein the lysed platelet composition has been formed by lysing a platelet concentrate, the platelet concentrate having a platelet concentration in the range of about $10^8$ platelets per ml to about $10^{12}$ platelets/ml.

Embodiment 18

The method of any preceding Embodiment, wherein the starting fibrin-containing material comprises entrained platelet membrane material, entrained platelet derived bioactive factors, or both.

Embodiment 19

The method of Embodiment 18, wherein the entrained platelet derived bioactive factors include fibrinogen, fibrin monomers, or both.

Embodiment 20

The method of Embodiment 18 or 19, wherein the fibrin hydrolysate material comprises entrained platelet membrane material, entrained bioactive platelet derived factors, or both.

Embodiment 21

The method of Embodiment 20, wherein the entrained platelet derived bioactive factors include fibrinogen, fibrin monomers, or both.

Embodiment 22

The method of any of Embodiments 9 to 11, wherein the fibrin starting material, fibrin hydrolysate material, and solid body comprise entrained platelet membrane material, entrained platelet derived bioactive factors, or both.

Embodiment 23

The method of Embodiment 22, wherein the platelet derived bioactive factors include fibrinogen, fibrin monomers, or both.

Embodiment 24

The method of any one of Embodiments 1 to 23, also comprising, after said subjecting, incubating the fibrin hydrolysate material in an aqueous medium for a period of time and under conditions that cause the fibrin hydrolysate material to swell.

Embodiment 25

The method of Embodiment 24, wherein said aqueous medium has a pH in the range of about 6 to about 8 and/or wherein said incubating is for a period of at least 1 hour.

Embodiment 26

The method of Embodiment 25, wherein said aqueous medium has a pH in the range of about 6.8 to about 7.5.

Embodiment 27

The method of any one of Embodiments 24 to 26, wherein said incubating causes the fibrin hydrolysate material to swell in volume.

Embodiment 28

The method of any one of Embodiments 24 to 27, also comprising, after said incubating, shearing the fibrin hydrolysate material.

Embodiment 29

The method of any one of Embodiments 24 to 27, wherein said incubating is conducted with the aqueous medium at a temperature in the range of about 0° C. to about 15° C.

Embodiment 30

The method of any of the preceding Embodiments, wherein the subjecting comprises contacting the fibrin starting material with a basic liquid medium having a pH greater than 9.

Embodiment 31

A medical hemostatic composition comprising a water-swellable fibrin hydrolysate, a water-swellable dialdehyde starch hydrolysate, or a combination thereof.

Embodiment 32

The composition of Embodiment 31, in the form of a dried solid or flowable gel.

Embodiment 33

The composition of Embodiment 32, in the form of a dried solid.

Embodiment 34

The composition of any of Embodiments 31 to 33, wherein the composition comprises a water-swellable fibrin hydrolysate, and wherein the water-swellable fibrin hydrolysate has not been crosslinked with a chemical crosslinker.

Embodiment 35

The composition of any of Embodiments 31 to 34, wherein the composition comprises a water-swellable fibrin hydrolysate, the composition also comprising at least one biologic polymer that is not fibrin, preferably wherein the biologic polymer is collagen.

Embodiment 36

The composition of Embodiment 34 or 35, comprising a decellularized, collagen-containing tissue material.

Embodiment 37

The composition of Embodiment 36, wherein the decellularized, collagen-containing tissue material is a decellularized membranous tissue.

Embodiment 38

The composition of Embodiment 37, wherein the decellularized membranous tissue comprises a submucosal extracellular matrix.

Embodiment 39

The composition of any one of Embodiments 36 to 38, wherein the collagen-containing tissue material is in particulate form.

Embodiment 40

The composition of any one of Embodiments 36 to 39, wherein the collagen-containing tissue material has been expanded by contact with a basic liquid medium.

Embodiment 41

The composition of any of Embodiments 36 to 39, wherein the collagen-containing tissue material is an expanded collagen-containing tissue material, wherein the expanded collagen-containing tissue material has been prepared by expanding a starting collagen-containing tissue material by contact with a basic liquid medium under conditions and for a period of time effective to expand the starting collagen-containing tissue material to provide the expanded collagen-containing tissue material, with the expanded collagen-containing tissue material having a volume that is at least 150% of that of the starting collagen-containing tissue material.

Embodiment 42

The composition of any one of Embodiments 36 to 41, wherein the water-swellable fibrin hydrolysate and collagen-containing tissue material are present at a weight ratio in the range of about 90:10 to about 10:90 on a dry weight basis.

Embodiment 43

The composition of Embodiment 42, wherein the water-swellable fibrin hydrolysate and collagen-containing tissue material are present at a weight ratio in the range of about 70:30 to about 30:70 on a dry weight basis.

Embodiment 44

The composition of Embodiment 43, wherein the water-swellable fibrin hydrolysate and collagen-containing tissue material are present at a weight ratio in the range of about 90:10 to about 40:60 on a dry weight basis.

Embodiment 45

The composition of any one of Embodiments 31 to 44, wherein the composition comprises a water-swellable fibrin hydrolysate, and wherein the water-swellable fibrin hydrolysate has been formed by hydrolyzing a fibrin clot material.

Embodiment 46

The composition of Embodiment 45, wherein the fibrin clot material has been formed by initiating clotting of a lysed platelet concentrate, preferably wherein the clotting is calcium-initiated clotting.

Embodiment 47

The composition of Embodiment 46, wherein the lysed platelet concentrate has been formed by lysing a platelet concentrate having a platelet concentration of about $10^7$ platelets per ml or greater.

Embodiment 48

The composition of any one of Embodiments 31 to 47, wherein the composition comprises a fibrin hydrolysate, the composition also comprising platelet membrane material, platelet derived bioactive factors, or both, from platelets from which fibrinogen was secreted in the formation of the fibrin.

Embodiment 49

The composition of any one of Embodiments 31 to 33, wherein the composition comprises a water-swellable dialdehyde starch hydrolysate.

Embodiment 50

The composition of Embodiment 49, wherein the composition also comprises a water-swellable fibrin hydrolysate.

Embodiment 51

The composition of Embodiment 50, wherein the water-swellable dialdehyde starch hydrolysate and the water-swellable fibrin hydrolysate are present in a dry weight ratio in the range of about 10:90 to about 90:10, more preferably in the range of about 30:70 to about 70:30.

Embodiment 52

The composition of any one of Embodiments 49 to 51, wherein the water-swellable dialdehyde starch hydrolysate has introduced carboxylic acid groups.

Embodiment 53

The composition of any one of Embodiments 49 to 52, wherein the water-swellable dialdehyde starch hydrolysate is dispersible in water.

Embodiment 54

The composition of any one of Embodiments 49 to 53, wherein the water-swellable starch hydrolysate has been prepared by a process comprising heating a starting dialdehyde starch material in an acidic aqueous medium.

Embodiment 55

The composition of Embodiment 54, wherein said heating a starting dialdehyde starch material in an acidic aqueous medium has been conducted for a period of time and at a temperature effective to swell the starting dialdehyde starch material to a volume that is at least two times an original volume of the starting dialdehyde starch material.

Embodiment 56

The composition of Embodiment 54 or 55, wherein said heating a starting dialdehyde starch material in an acidic aqueous medium is effective to provide the dialdehyde starch hydrolysate material having an increased dispersibility in water relative to the starting dialdehyde starch material.

Embodiment 57

The composition of any one of Embodiments 54 to 56, wherein said heating a starting dialdehyde starch material is effective to provide the dialdehyde starch hydrolysate having a lower weight average molecular weight than the starting dialdehyde starch material.

Embodiment 58

The composition of any one of Embodiments 54 to 57, wherein said heating a starting dialdehyde starch material in an acidic aqueous medium is effective to provide the dialdehyde starch hydrolysate having a higher amount of carboxylic acid groups than the starting dialdehyde starch material.

Embodiment 59

The composition of any one of Embodiments 54 to 58, wherein said heating a starting dialdehyde starch material in an acidic aqueous medium is effective to provide the dialdehyde starch hydrolysate having a lower amount of aldehyde groups than the starting dialdehyde starch material.

Embodiment 60

The composition of any one of Embodiments 54 to 59, wherein said heating a starting dialdehyde starch material in an acidic aqueous medium is effective to provide the dialdehyde starch hydrolysate having a particle size in aqueous suspension that is less than that of the starting dialdehyde starch material.

Embodiment 61

A method for inducing hemostasis in a patient, comprising applying to a site of bleeding in the patient the composition of any one of Embodiments 31 to 60, or 80.

Embodiment 62

A method for making a hemostasis promoting material, comprising:
subjecting a starting dialdehyde starch material to a heated aqueous medium so as to form a dialdehyde starch hydrolysate material.

Embodiment 63

The method of Embodiment 62, wherein the heated aqueous medium has an acidic pH.

Embodiment 64

The method of Embodiment 63, wherein the pH is less than 5.

Embodiment 65

The method of any one of Embodiments 62 to 64, wherein the aqueous medium comprises aqueous hydrochloric acid, aqueous sulfuric acid, aqueous phosphoric acid, or aqueous carboxylic acid.

Embodiment 66

The method of any one of Embodiments 62 to 65, wherein said subjecting is effective to swell the starting dialdehyde starch material to a volume that is at least two times an original volume of the starting dialdehyde starch material.

Embodiment 67

The method of any one of Embodiments 62 to 66, wherein said subjecting is effective to provide the dialdehyde starch hydrolysate material having an increased dispersibility in deionized water relative to the starting dialdehyde starch material.

Embodiment 68

The method of any one of Embodiments 62 to 67, wherein said subjecting is effective to provide the dialdehyde starch hydrolysate material having a lower weight average molecular weight than the starting dialdehyde starch material.

Embodiment 69

The method of any one of Embodiments 62 to 68, wherein said subjecting is effective to provide the dialdehyde starch hydrolysate material having a higher amount of carboxylic acid groups than the starting dialdehyde starch material.

Embodiment 70

The method of any one of Embodiments 62 to 69, wherein said subjecting is effective to provide the dialdehyde starch hydrolysate material having a lower amount of aldehyde groups than the starting dialdehyde starch material.

Embodiment 71

The method of any one of Embodiments 62 to 70, wherein said subjecting is effective to provide the dialdehyde starch hydrolysate material having a decreased particle size in aqueous suspension relative to the starting dialdehyde starch material.

Embodiment 72

The method of any one of Embodiments 62 to 71, also comprising:
packaging the dialdehyde starch hydrolysate material in a package; and
terminally sterilizing the dialdehyde starch hydrolysate material in the package.

Embodiment 73

The method of any one of Embodiments 62 to 72, also comprising:
drying the dialdehyde starch hydrolysate.

Embodiment 74

The method of any one of Embodiments 62 to 72, also comprising:
charging a preparation including the dialdehyde starch hydrolysate and liquid to a mold; and
drying the preparation in the mold to form a molded body.

Embodiment 75

The method of Embodiment 74, wherein the molded body comprises a foam including the dialdehyde starch hydrolysate.

Embodiment 76

The method of Embodiment 74 or 75, wherein the preparation also includes at least one polymeric material other than the dialdehyde starch hydrolysate.

Embodiment 77

The method of Embodiment 76, wherein said at least one polymeric material comprises a protein.

Embodiment 78

The method of Embodiment 77, wherein the protein is fibrin or a fibrin hydrolysate.

Embodiment 79

The method of any one of Embodiments 74 to 78, wherein said drying comprises lyophilizing.

Embodiment 80

The composition of any one of Embodiments 31 to 60, wherein the water-swellable fibrin hydrolysate is a water-insoluble, water-swellable fibrin hydrolysate, and wherein the water-swellable dialdehyde starch hydrolysate is a water-insoluble, water-swellable fibrin hydrolysate.

The uses of the terms "a" and "an" and "the" and similar references in the context of describing the invention (especially in the context of the following claims) are to be construed to cover both the singular and the plural unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A medical hemostatic composition comprising a water-swellable fibrin hydrolysate prepared by hydrolysis of a fibrin material so as to provide the fibrin hydrolysate having a sorptive capacity for water at pH 7 at 20° C. that is at least two times that of the fibrin material.

2. The composition of claim 1, in the form of a dried solid or flowable gel.

3. The composition of claim 2, in the form of a dried solid.

4. The composition of claim 1, wherein the water-swellable fibrin hydrolysate has not been crosslinked with a chemical crosslinker.

5. The composition of claim 1, wherein the composition further comprises a water-swellable dialdehyde starch hydrolysate.

6. A method for inducing hemostasis in a patient, comprising applying to a site of bleeding in the patient the composition of claim 1.

7. The composition of claim 1, further comprising at least one biologic polymer that is not fibrin.

8. The composition of claim 4, further comprising a decellularized, collagen-containing tissue material.

9. The composition of claim 8, wherein the decellularized, collagen-containing tissue material is a decellularized membranous tissue.

10. The composition of claim 9, wherein the decellularized membranous tissue comprises a submucosal extracellular matrix.

11. The composition of claim 8, wherein the collagen-containing tissue material is in particulate form.

12. The composition of claim 8, wherein the collagen-containing tissue material has been expanded by contact with a basic liquid medium.

13. The composition of claim 8, wherein the collagen-containing tissue material is an expanded collagen-containing tissue material, wherein the expanded collagen-containing tissue material has been prepared by expanding a starting collagen-containing tissue material by contact with a basic liquid medium under conditions and for a period of time effective to expand the starting collagen-containing tissue material to provide the expanded collagen-containing tissue material, with the expanded collagen-containing tissue material having a volume that is at least 150% of that of the starting collagen-containing tissue material.

14. The composition of claim 8, wherein the water-swellable fibrin hydrolysate and collagen-containing tissue material are present at a weight ratio in the range of about 90:10 to about 10:90 on a dry weight basis.

15. The composition of claim 14, wherein the water-swellable fibrin hydrolysate and collagen-containing tissue material are present at a weight ratio in the range of about 70:30 to about 30:70 on a dry weight basis.

16. The composition of claim 15, wherein the water-swellable fibrin hydrolysate and collagen-containing tissue material are present at a weight ratio in the range of about 90:10 to about 40:60 on a dry weight basis.

17. The composition of claim 1, wherein the water-swellable fibrin hydrolysate comprises a fibrin clot material.

18. The composition of claim 17, wherein the fibrin clot material has been formed by initiating clotting of a lysed platelet concentrate.

19. The composition of claim 18, wherein the lysed platelet concentrate has been formed by lysing a platelet concentrate having a platelet concentration of about $10^7$ platelets per ml or greater.

20. The composition of claim 1, wherein the composition further comprises platelet membrane material, platelet derived bioactive factors, or both, from platelets from which fibrinogen was secreted in the formation of the fibrin material.

21. The composition of claim 5, wherein the water-swellable dialdehyde starch hydrolysate and the water-swellable fibrin hydrolysate are present in a dry weight ratio in the range of about 10:90 to about 90:10, more preferably in the range of about 30:70 to about 70:30.

22. The composition of claim 5, wherein the water-swellable dialdehyde starch hydrolysate has introduced carboxylic acid groups.

23. The composition of claim 5, wherein the water-swellable dialdehyde starch hydrolysate is dispersible in water.

24. The composition of claim 5, wherein the water-swellable starch hydrolysate has been prepared by a process comprising heating a starting dialdehyde starch material in an acidic aqueous medium.

* * * * *